US00PP22825P3

(12) United States Plant Patent

Henny et al.

(10) Patent No.: US PP22,825 P3

(45) Date of Patent: Jun. 26, 2012

(54) *AGLAONEMA* PLANT NAMED 'UF-808-4'

(50) Latin Name: *Aglaonema commutatum*
Varietal Denomination: UF-808-4

(75) Inventors: Richard Henny, Tavares, FL (US); Jianjun Chen, Apopka, FL (US)

(73) Assignee: Florida Foundation Seed Producers, Inc., Greenwood, FL (US)

( * ) Notice: Subject to any disclaimer, the term of this patent is extended or adjusted under 35 U.S.C. 154(b) by 296 days.

(21) Appl. No.: 12/799,315

(22) Filed: Apr. 21, 2010

(65) Prior Publication Data

US 2011/0265232 P1 Oct. 27, 2011

(51) Int. Cl.
*A01H 5/00* (2006.01)

(52) U.S. Cl. ..... Plt./376

(58) Field of Classification Search ..... Plt./376
See application file for complete search history.

(56) References Cited

U.S. PATENT DOCUMENTS

| | | | | |
|---|---|---|---|---|
| PP7,634 | P * | 8/1991 | Frazer | Plt./376 |
| PP12,867 | P2 * | 8/2002 | Henny | Plt./376 |
| PP12,985 | P2 * | 9/2002 | Mukundan et al. | Plt./376 |
| PP20,463 | P2 * | 11/2009 | Henny et al. | Plt./376 |
| 2002/0133861 | P1 * | 9/2002 | Mukundan et al. | Plt./376 |

OTHER PUBLICATIONS

Anonymous. "*Aglaonema*—Florida Foundation Seed Producers, Inc." Available at http://ffsp.net/aglaonema.html accessed Oct. 1, 2011, see particularly pp. 4 and 5.*

Henny, Richard J. and Jianjun Chen. "'Scenic Bay' *Aglaonema*". HortScience 45(8): 1281-1282. 2010.*

* cited by examiner

*Primary Examiner* — Wendy C Haas

(57) ABSTRACT

A new and distinct variety of *Aglaonema* plant, denominated 'UF-808-4', characterized by medium sized and upright plant growth habit, vigorous and dense growth habit, dark green-colored leaves with large grey green-colored venal areas covering over half the leaf surface, and petioles and stems possessing numerous white spots.

2 Drawing Sheets

Figure 1:
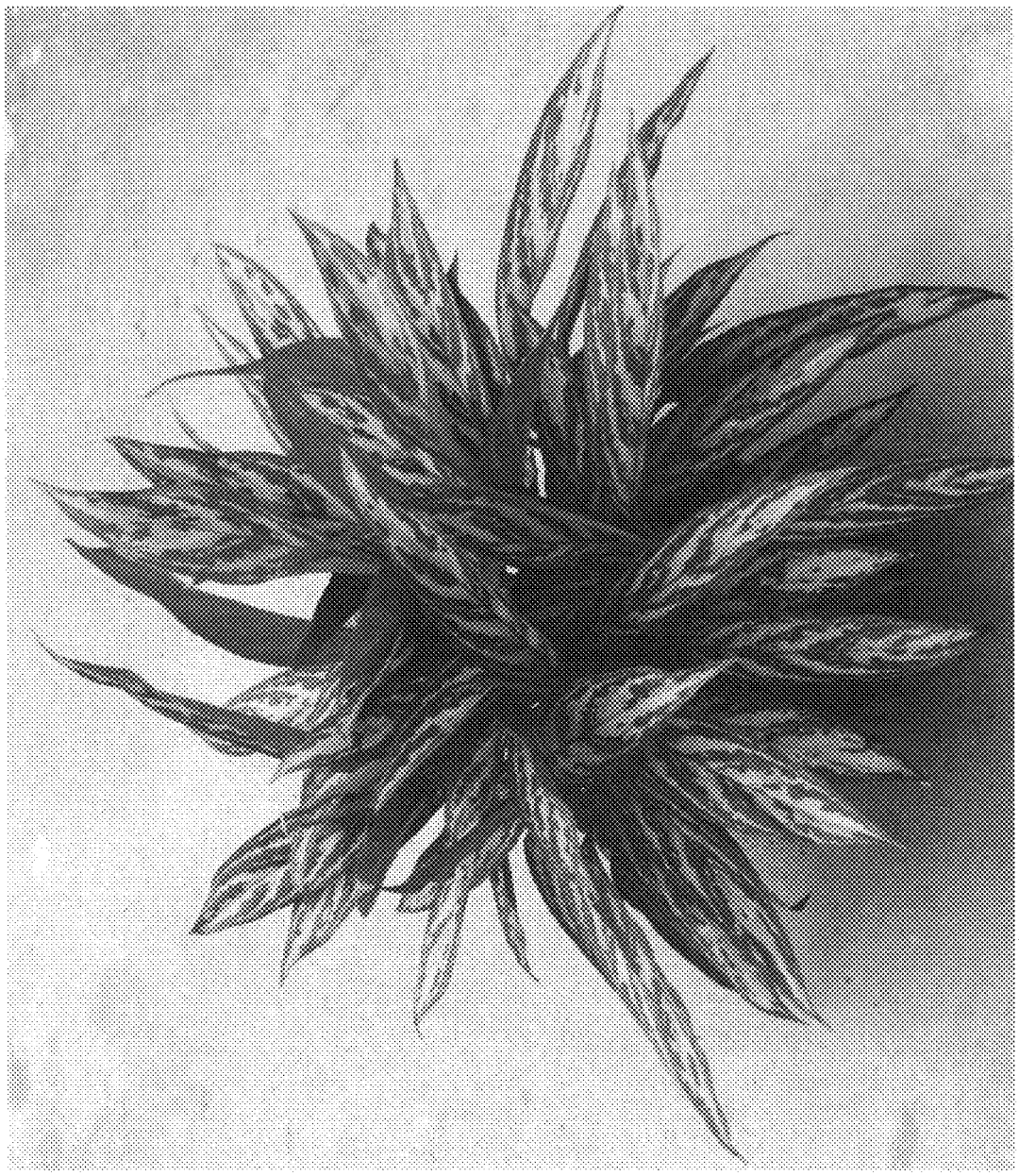
Figure 2:
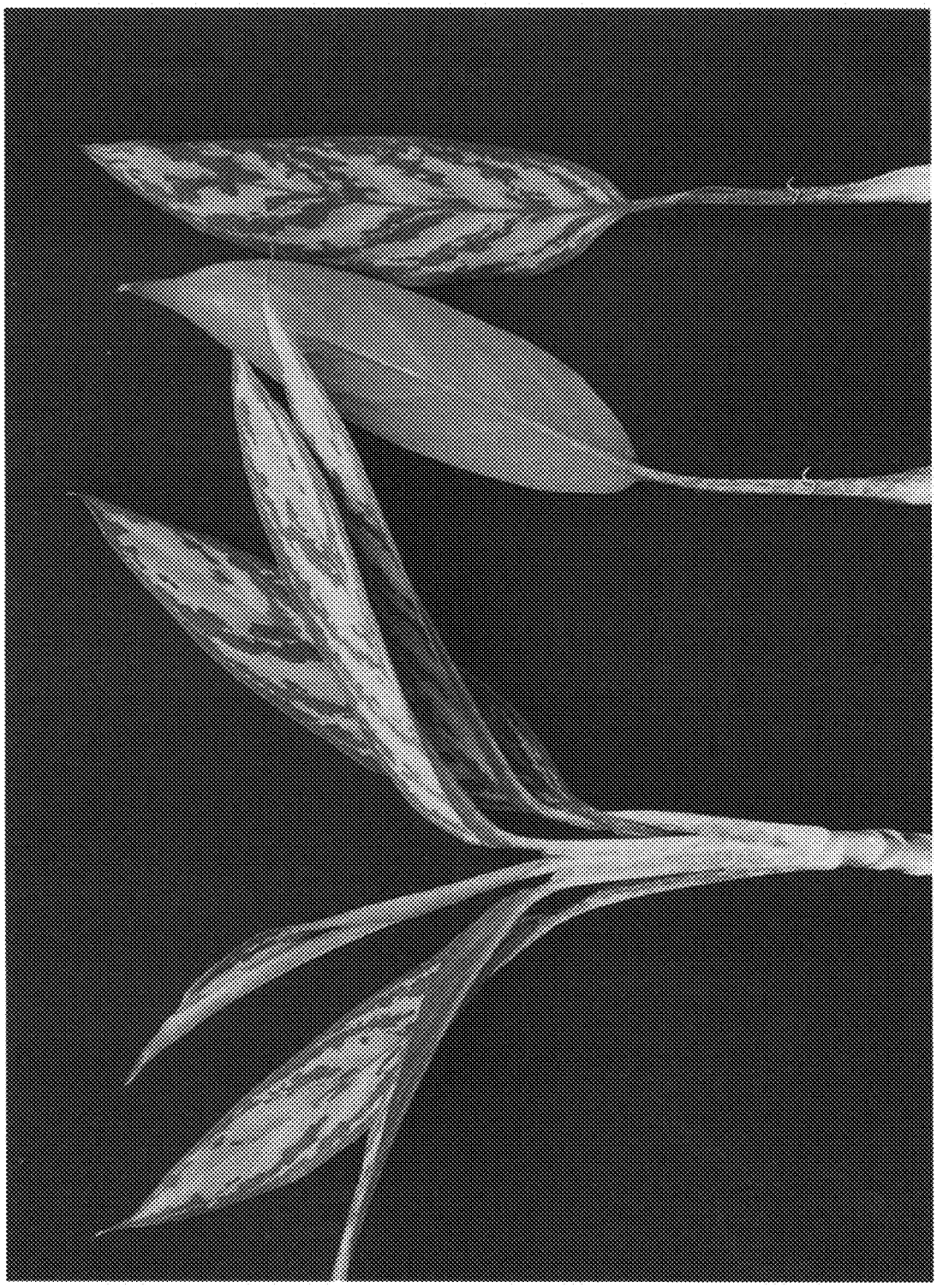

Genus and species: *Aglaonema commutatum.*
Variety denomination: 'UF-808-4'.

CROSS REFERENCE TO RELATED APPLICATIONS

The present application is related to U.S. Plant Pat. No. 20,463, "*Aglaonema* Plant Named 'UF-742-3'".

BACKGROUND OF THE NEW PLANT

The present invention relates to a new and distinct cultivar of *Aglaonema* plant, botanically known as *Aglaonema commutatum,* and hereinafter referred to by the name 'UF-808-4'.

The objective of the Inventor's breeding program is to create new *Aglaonema* cultivars that have uniform plant habit, exceptional performance and unique and attractive foliage coloration.

The new *Aglaonema* originated from a cross-pollination made by the Inventors in Apopka, Fla. of *Aglaonema commutatum* cultivar 'Curtissii', not patented, as the female, or seed parent and *Aglaonema commutatum* cultivar 'Treubii', not patented, as the male, or pollen parent. The new *Aglaonema* was discovered and selected by the Inventors as a single plant within the progeny of the stated cross-pollination in a controlled environment in Apopka, Fla.

Asexual reproduction of the new cultivar by tip cuttings in a controlled environment in Apopka, Fla. has shown that the unique features of this new *Aglaonema* are stable and reproduced true to type in successive generations of asexual reproduction.

SUMMARY OF THE INVENTION

The cultivar 'UF-808-4' has not been observed under all possible environmental conditions. The phenotype may vary somewhat with variations in environment such as temperature and light intensity, without, however, any variance in genotype.

The following traits have been repeatedly observed and are determined to be the unique characteristics of 'UF-808-4'. There characteristics in combination distinguish 'UF-808-4' as a new and distinct cultivar of *Aglaonema:*

1. Medium sized and upright plant growth habit.
2. Vigorous and dense growth habit.
3. Dark green-colored leaves with large grey green-colored venal areas covering over half the leaf surface.
4. Petioles and stems possess numerous white spots.

Plants of the new *Aglaonema* differ from plants of the female parent selection, the cultivar 'Curtissii', in the following characteristics:

1. Plants of the new *Aglaonema* have a different variegation pattern than the female parent.
2. Plants of the new *Aglaonema* are smaller and more compact than the female parent selection.
3. Plants of the new *Aglaonema* produce leaves that are narrower and shorter than the female parent.
4. Plants of the new *Aglaonema* have spotted petioles whereas plants of the female parent have green petioles.

Plants of the new *Aglaonema* differ from plants of the male parent, the cultivar 'Treubii', in the following characteristics:

1. Plants of the new *Aglaonema* have a different variegation pattern than the male parent.
2. Plants of the new *Aglaonema* have leaves that are wider than the male parent.
3. Plants of the new *Aglaonema* are more compact than the male parent.

4. Plants of the new *Aglaonema* have different colored petioles than the male parent.

Plants of the new *Aglaonema* can also be compared to plants of the cultivar 'Emerald Bay', U.S. Plant Pat. No. 12,867. In side-by-side comparisons conducted in Apopka, Fla., plants of the new *Aglaonema* differed from plants of the cultivar 'Emerald Bay' in the following characteristics:

1. Plants of the new *Aglaonema* were smaller than plants of the cultivar 'Emerald Bay'.
2. Plants of the new *Aglaonema* had smaller and narrower leaves than plants of the cultivar 'Emerald Bay'.
3. Plants of the new *Aglaonema* had a shorter canopy height but a wider canopy width than the cultivar 'Emerald Bay'.

DESCRIPTION OF THE PHOTOGRAPHS

The accompanying photographs show the overall appearance of the new *Aglaonema*. These photographs show the colors as true as it is reasonably possible to obtain in colored reproductions of this type. Colors in the photographs may differ slightly from the color values cited in the detailed botanical description which accurately describe the colors of the new *Aglaonema*.

The photograph on the first sheet is a side perspective view of a typical plant of 'UF-808-4' grown in a container.

The photograph on the second sheet is a close-up view of a typical stem and individual leaves showing the upper and lower leaf surfaces of 'UF-808-4'.

Plants were grown from a single stem cutting and were approximately 9 months old when the photographs were taken.

DESCRIPTION OF THE NEW CULTIVAR

In the following description, color references are made to The Royal Horticultural Society Colour Chart, 1995 Edition, except where general terms of ordinary significance are used. The aforementioned photographs and following observations and measurements describe plants grown in containers in Apopka, Fla. during the spring and early summer in a glass-covered greenhouse. Plants were grown using practices and under conditions which approximate those generally used in commercial *Aglaonema* production. During the production of the plants, day temperature ranged from about 28° C. to 33° C., night temperature ranged from about 18° C. to 25° C. and light levels were about 2,500 foot-candles. Plants were grown from a single stem cutting and were approximately 9 months old when the detailed description was taken.

DETAILED BOTANICAL DESCRIPTION

Classification:

*Botanical.*—*Aglaonema commutatum.*

*Common name.*—*Aglaonema.*

*Parentage.*—Female, or seed parent: *Aglaonema commutatum* cultivar 'Curtissi', not patented. Male, or pollen parent: *Aglaonema commutatum* cultivar 'Treubii', not patented.

*Propagation.*—Type: By tip cuttings. Time to initiate roots, summer: About 20-24 days at 25° C. to 35° C. Time to initiate roots, winter: About 25-32 days at 15° C. to 27° C. Time to produce a rooted young plant, summer: About 30-35 days at 25° C. to 35° C. Time to produce a rooted young plant, winter: About 40-45 days at 15° C. to 27° C. Root description: Abundant fleshy whitish-colored roots with finer lateral roots.

Plant description:

*Plant/growth habit.*—Short compact plant habit; inverted triangle. Vigorous, dense growth habit; suitable for 15-cm to 20-cm containers. New leaves initially upright and then pointing outwardly with development.

*Plant height, from soil level to top of leaf canopy plane.*—About 25 cm to 30 cm.

*Plant diameter or spread.*—About 40 cm to 48 cm.

Stem description:

*Branching habit.*—Plants of the new *Aglaonema* are freely basal branching with about 8 to 10 basal branches developing per plant.

*Aspect.*—Mostly upright.

*Strength.*—Strong.

*Length, soil level to junction of two youngest leaves.*—15 cm to 18 cm.

*Diameter.*—About 1.5 cm.

*Internode length.*—About 7 mm to 9 mm.

*Color, immature.*—137C mottled with 148C and 148D.

*Color, mature.*—151C mottled with 148C and 148D; with further development, 153C to 153D mottled with 148C and 148D.

Foliage description:

*Arrangement.*—Alternate/whorled; simple.

*Length.*—About 17 to 22 cm.

*Width (flattened).*—About 3.3 cm to 3.9 cm.

*Shape.*—Lanceolate.

*Apex.*—Sharply acuminate.

*Base.*—Obtuse.

*Margin.*—Entire; mostly flat with some broad undulations.

*Texture.*—Upper and lower surfaces: Smooth, glabrous.

*Venation pattern.*—Pinnate.

*Color.*—Developing leaves, upper surface: Ground color, between 137B to 137C; venal areas 191B to 191C. Venation: Midrib 137A to 137B; primary veins 137A. Developing leaves, lower surface: Ground color 138B uniform'. Venation: Midrib 138B; primary veins 138D. Fully expanded leaves, upper surface: Ground color, 139A, venal areas, 191A to 191B. Venation: Midrib 191A in basal half, fading to 138B near the apex; primary veins 191C. Fully expanded leaves, lower surface: Ground color, 137C; venal areas mottled with 155A to 155B. Venation: Midrib 155A to 155B, mottling associated with edges of midrib 155A to 155B; primary veins 155A to 155B.

*Petiole.*—Aspect: Mostly erect, arching outwardly to about 30° from vertical with development. Length: 8.5 to 9.5 cm. Diameter, distal: about 3 mm. Diameter, proximal, flattened: About 2 cm. Strength: Strong: flexible. Color, distal: 155A to 155B. Color, proximal: 155A; area adjacent to stem, 155D often faintly tinged with 138A. Wing length: About 6 cm. Wing diameter, base: About 1 cm. Wing color, inner surface: 155A. Wing color, outer surface: 155A; area adjacent to stem, 155A often faintly tinged with 138A.

Inflorescence description: The inflorescence consists of a spathe and spadix. Inflorescences occur sporadically in clusters of 4-5 near the shoot apex.

*Spathe.*—Length: 7 cm to 8 cm. Width: 2 cm to 3 cm. Color, immature; outer surface: 149D, inner surface 149D. Color, mature; outer surface: 149D, inner surface 149D.

*Spadix.*—Length: About 3 cm to 4 cm; Female section: About 4 mm to 6 mm; Male section: About 3.0 to 3.5 cm. Width: About 4 mm to 5 mm. Color: lower female section; stigmatic surface 15D to 15C; outer ovary surface 149D. Each spadix contains about 5 to 7 individual female flowers. Color: upper male section; 158A.

*Peduncle.*—Length: About 5 cm to 6 cm. Diameter: About 2 mm to 3 mm. Color: 139D.

The new *Aglaonema* is apparently sterile, since no pollen has been produced on any of several inflorescences observed and no seed has been produced following controlled pollinations.

Disease/pest resistance: No unusual resistance or susceptibility to insects and diseases noted.

Temperature tolerance: Plants of the new *Aglaonema* have been observed to be tolerant to temperatures ranging from about 13° C. to about 40° C. for several hours.

We claim:

1. A new and distinct cultivar of *Aglaonema* plant as shown and described herein.

* * * * *